United States Patent

Cooper et al.

Patent Number: 5,916,873
Date of Patent: Jun. 29, 1999

[54] TEICOPLANIN DERIVATIVES

[75] Inventors: Robin David Grey Cooper, Indianapolis; Nancy June Snyder, Charlottesville, both of Ind.

[73] Assignee: Eli Lilly and Company, Indianapolis, Ind.

[21] Appl. No.: 09/053,848

[22] Filed: Apr. 1, 1998

Related U.S. Application Data

[60] Provisional application No. 60/042,017, Apr. 17, 1997.
[51] Int. Cl.$^6$ .......................... A61K 38/00; A61K 38/12; C07K 16/00; C07K 17/00
[52] U.S. Cl. ..................................... 514/9; 514/8; 514/11; 530/317
[58] Field of Search ................................ 530/317; 514/9, 514/11

[56] References Cited

FOREIGN PATENT DOCUMENTS

| 0 204 179 A1 | 5/1986 | European Pat. Off. . |
| 0 306 645 A2 | 6/1988 | European Pat. Off. . |
| 0 351 684 A2 | 1/1990 | European Pat. Off. . |
| 0 351 685 A2 | 1/1990 | European Pat. Off. . |
| 0 352 538 A2 | 1/1990 | European Pat. Off. . |

*Primary Examiner*—Cecilia J. Tsang
*Assistant Examiner*—S. G. Marshall
*Attorney, Agent, or Firm*—Arlene K. Musser

[57] ABSTRACT

The present invention is directed to teicoplanin derivatives of the following general formula, wherein $R^1$ and $R^2$ are as defined in the specification.

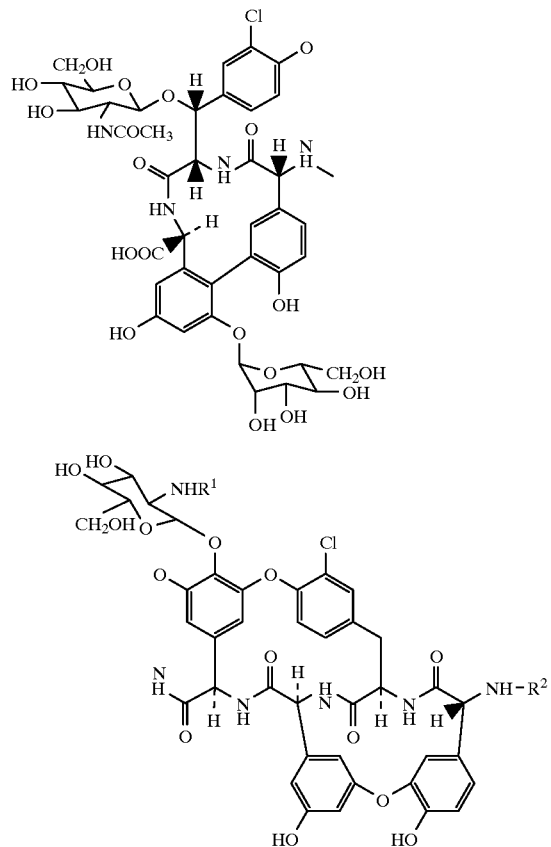

These derivatives are useful as antibiotics for the control of gram-positive bacteria.

9 Claims, No Drawings

TEICOPLANIN DERIVATIVES

CROSS REFERENCE

This application claims priority of Provisional Application Ser. No. 60/042,017, filed Apr. 17, 1997.

BRIEF SUMMARY OF THE INVENTION

The present invention is directed to derivatives of teicoplanin, which is an antibiotic of the glycopeptide family, more particularly of the ristocetin type.

DETAILED DESCRIPTION OF THE INVENTION

The present invention is directed to compounds of the formula:

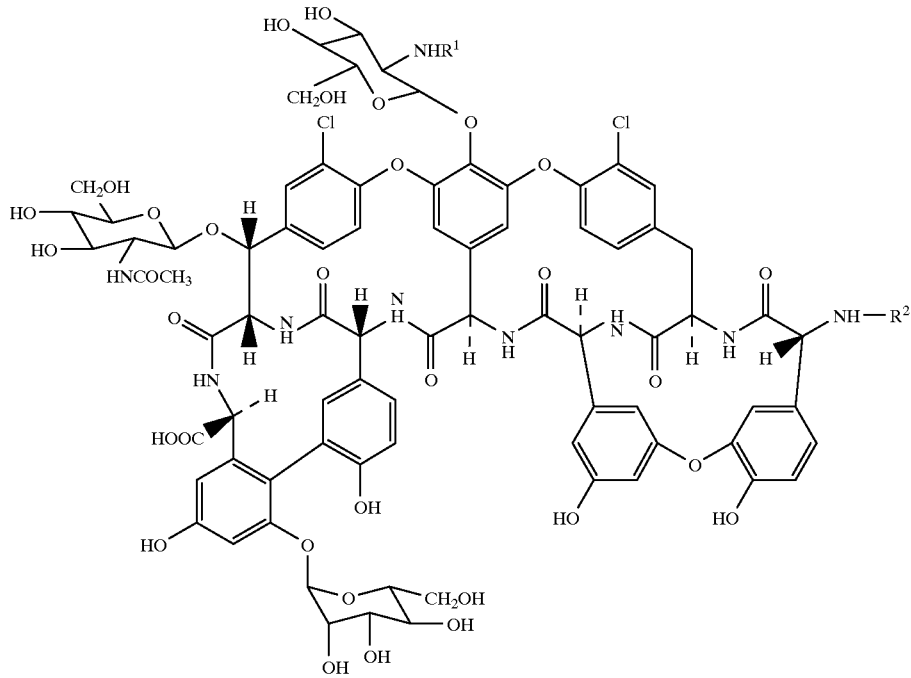

and the pharmaceutically acceptable salts thereof. In the foregoing formula, one of $R^1$ and $R^2$ is: —$CH_3$, —$CH_2$—($C_1$–$C_{11}$ alkyl), —$CH_2$—($C_2$–$C_{11}$ alkenyl), —$CH_2$—($C_2$–$C_{11}$ alkynyl), cycloalkylmethyl of the formula:

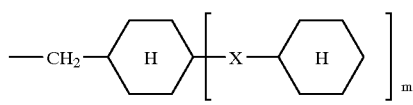

naphthylmethyl,
thienylbenzyl,
phenylthienylmethyl,
benzyl of the formula:

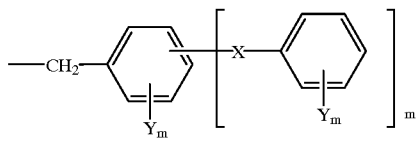

wherein X is a linker of the formula —$(CH_2)_x$—Z—$(CH_2)_y$—,
wherein each of x and y is 0–6, and the sum of x and y=0–6,
and Z is a bond, —O—, —S—, —CH=CH—, or —C≡C—;

and any Y is independently halo, loweralkyl of $C_1$–$C_5$, loweralkoxy of $C_1$–$C_5$, loweralkylthio of $C_1$–$C_5$, trifluoromethyl, or trifluoromethoxy, and each m is independently 0 or 1;

and the other of $R^1$ and $R^2$ is identical or is H, or, in the case of $R^2$, an amino protecting group.

Any alkyl, alkenyl, or alkynyl can be straight chain or branched.

The foregoing compounds are active as antibiotics, and in particular exhibit activity against gram-positive organisms, including activity against vancomycin-resistant enterococci ("VRE").

The present compounds are prepared by the reaction of deacyl teicoplanin, having the following formula:

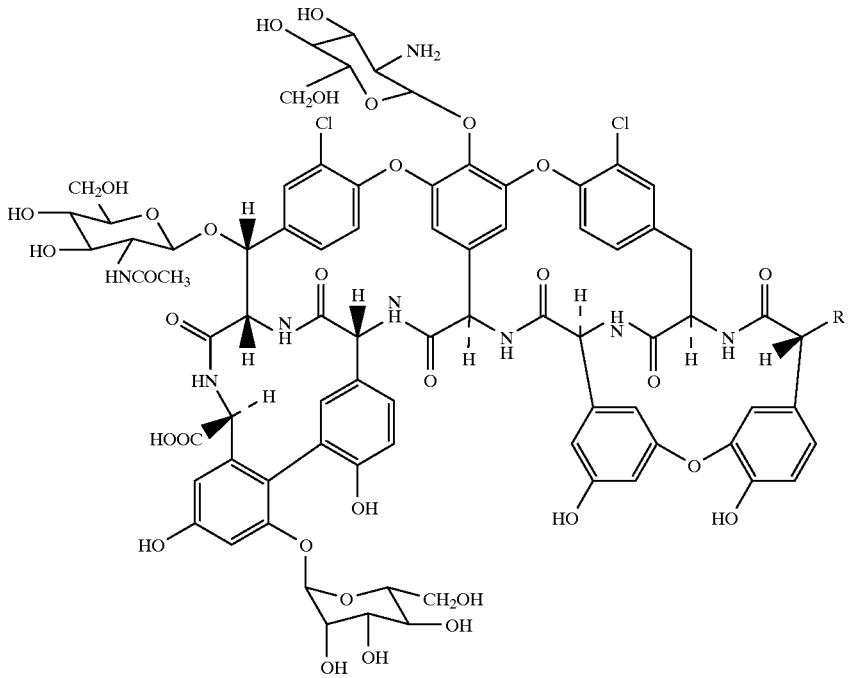

wherein R is amino or protected amino. Deacyl teicoplanin is prepared by deacylating teicoplanin. Teicoplanin is a known antibiotic, having five factors differing only as to the identity of the acyl on the amine on the $N^4$-sugar. Deacyl teicoplanin is prepared from teicoplanin or teicoplanin wherein the $N^{15}$ amine has been protected. Amino protection and amino protecting groups are well known. See column 6 of U.S. Pat. No. 5,099,015, which is incorporated herein by reference. Special attention is directed to the references there cited, J. S. Barton, "Protective Groups in Organic Chemistry", J. G. W. McOmie, Ed., Plenum Press, New York, N.Y., 1973, Chapter 2; and T. W. Greene, "Protective Groups in Organic Synthesis," John Wiley and Sons, New York, N.Y., 1981, Chapter 7.

The teicoplanin or $N^{15}$-protected teicoplanin is reacted with a deacylating enzyme known as echinochandin B esterase ("ECB esterase"). This reaction is illustrated below in Preparation 1. The production of ECB esterase is described in U.S. Pat. Nos. 4,293,482 and 4,304,716, which are incorporated herein by reference. Other references regarding ECB deacylase, also incorporated herein by reference, include U.S. Pat. No. 5,573,936; Appl. Microbiol. Biotechnol. (1993) 39:532–536; and international patent application PCT/US95/08832.

The reaction of deacyl teicoplanin to prepare the compounds of the present invention is a reductive alkylation, and is conducted in accordance with known techniques. In general, the reaction consists of reacting deacyl teicoplanin, or a salt thereof, with an aldehyde to form a Schiff's base, which is then reduced to the desired alkylated product. The reducing agent may be added simultaneously with the deacyl teicoplanin and the aldehyde. Whether carried out sequentially or simultaneously, the reaction is carried out in a polar solvent such as DMF, methanol, on a mixture of DMF and methanol and at temperatures of from 25° to 100° C., preferably at temperatures of from 60° to 70° C., employing equimolar amounts or a slight excess of aldehyde. The reducing agent is also preferably employed in excess. A source of soluble copper may be added to the reaction mixture, as illustrated in Examples 2 and 3 below. Copper (II) acetate is a preferred source of copper. The copper is preferably supplied in an amount equimolar with the deacyl teicoplanin.

The compounds of the present invention form salts. These salts are readily prepared by conventional methods well known to those skilled in the art. Pharmaceutically acceptable salts are preferred. Any $N^{15}$-protecting group can likewise be removed in conventional methods.

Disubstituted compounds, those wherein $R^2=R^1$, are preferred. Also preferred are compounds where $R^1$, or both $R^1$ and $R^2$, represent

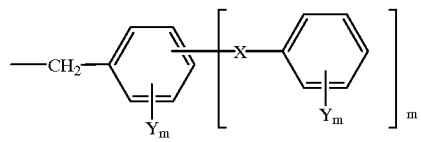

as defined.

The following examples illustrate the present invention and will enable those skilled in the art to practice the invention.

Preparation 1

Deacyl Teicoplanin

A crude preparation of ECB deacylase determined to contain approximately 15,000 mU of deacylating activity (1.3 liters) was adjusted to pH 7.5 with concentrated ammonium hydroxide. Teicoplanin (1 gram) was added to this enzyme solution maintaining pH at 7.5 with base. Temperature was maintained at 26° C. and pH was maintained at 7.5 by adding 1N ammonium hydroxide or 1N hydrochloric acid. After 17 hours under these conditions, HPLC analysis of the reaction mixture indicated that approximately 70% of the teicoplanin was hydrolyzed. HPLC data indicated that additional reaction time under the conditions stated above did not improve yield. The hydrolysis of teicoplanin was monitored by HPLC utilizing a gradient eluent system at 1.0 ml min$^{-1}$ on a Waters RCM 8×10 RadialPak containing a NovaPak C18 column cartridge with a μBondaPak C18 guard column with a detection at 280 nm. Gradient system was as follows: 0.2% aqueous trifluoroacetic acid/acetonitrile (95/5, v/v) held for 3 minutes, ran 17 minute linear gradient to 0.2% aqueous trifluoroacetic acid/acetonitrile (60/40, v/v), then ramped down to 0.2% aqueous trifluoroacetic acid/acetonitrile (95/5, v/v) in 5 minutes. A second 1 gram reaction was conducted as described above.

EXAMPLE 1

Deacyl Teicoplanin, Bis(4-phenylbenzyl) Derivative

A mixture of deacyl teicoplanin trifluoracetic acid salt, (0.051 g, 0.0295 mmol, 1.0 eq.) in DMF (5 mL) under an atmosphere of argon was treated with 4-biphenylcarboxaldehyde (0.0066 mg, 0.0324 mmol, 1.1 eq.). The resulting mixture was heated to 70° and maintained as such for 2 hours. The solution was then treated with sodium cyanoborohydride (0.0022 mg, 0.0324 mmol, 1.1 eq.). Heating at 70° was continued for an additional 2 hours after which the mixture was stirred at room temperature overnight, diluted with water (25 mL), and lyophilized to give a solid. The solid was purified by preparative reverse-phase high performance liquid chromatography (HPLC) using a Waters 3×(40×100 mm) C18 Nova-Pak cartridge with Waters C18 Nova-pak guard insert and utilizing a TFA buffer system. The TFA system consisted of 15% $CH_3CN$/0.1% TFA at time zero to 45% $CH_3CN$/0.1% TFA at 28 min. The analytical method for analysis was accomplished by using a Waters C18 Nova-pak RCM column (8×100 mm) with a Nova-pak C18 guard insert, eluting with a 2.0 mL/minute linear gradient of 95% TEAP/5% $CH_3CN$ at time=0) to 20% TEAP/80% $CH_3CN$ at time=30 minutes (TEAP=0.5% aqueous triethylamine adjusted to pH=3 with phosphoric acid). The fraction containing the product was detected by ultraviolet scan at 235 nm. The organic solvent was removed and the product lyophilized to give the deacylteicoplanin, bis(4-phenylbenzyl) derivative, as the trifluoracetic acid salt, a white solid (0.018 g, 30%).

EXAMPLES 2 AND 3

Deacyl Teicoplanin, $N^{15}$-(4-phenylbenzyl) Derivative and

Deacyl Teicoplanin, $N^{Glu}$-(4-phenylbenzyl) Derivative

A mixture of deacyl teicoplanin trifluoracetic acid salt, (0.048 g, 0.0281 mmol, 1.0 eq.), in 1:1 DMF/methanol (4 ml) and copperdiacetate (0.0058 mg, 0.0292 mmol, 1.04 eq.) was stirred together at room temperature for 10 minutes. The solution was then treated with 4-biphenylcarboxaldehyde (0.0061 mg, 0.0337 mmol, 1.2 eq.) and sodium cyanoborohydride (0.0021 mg, 0.0337 mmol, 1.2 eq.) and heated to 70° C. for approximately 18 hours. The mixture was concentrated in vacuo.

The solid was purified by HPLC as in Example 1 and three products were isolated: (1) monoalkylated product on the N-terminus ($R^2$=4-phenylbenzyl), as a white solid (0.007 g, 4%); (2) monoalkylated on the glucosamine ($R^1$=4-phenylbenzyl), as a white solid (0.002 g, 4%); and (3) dialkylated product ($R^1$=$R^2$=4-phenylbenzyl) as in Example 1.

EXAMPLE 4

Deacyl Teicoplanin, Bis(10-undecen-1-yl) Derivative

A mixture of deacyl teicoplanin trifluoracetic acid salt, (0.076 g, 0.0423 mmol, 1.0 eq.), in 6 mL DMF was treated with undecylenic aldehyde (0.016 g, 0.0924 mmol, 2.1 eq.) and sodium cyanoborohydride (0.006 g, 0.0888 mmol, 2.1 eq.). The mixture was stirred at 70° for 2 hours and stirred at room temperature overnight. The mixture was diluted with water (25 mL) and lyophilized to give a solid. The solid was purified by HPLC as in method A. A decyl teicoplanin, bis(10-undecen-1-yl) derivative product was isolated as the trifluoracetic acid salt, a white solid (0.0085 g, 9.6%).

Data on the foregoing compounds, and other compounds representative of the present invention, are presented in the following table.

TABLE 1

| Ex # | $R^1$ | Method of Ex # | Mass Spec | HPLC Reten. time | % Yield | $R^2$ |
|---|---|---|---|---|---|---|
| 1 | 4-phenylbenzyl | 1 | 2058, M + 2 | 9.57 | 30 | =$R^1$ |
| 2 | H | 2 | 1892, M + 3 | 7.74 | 13 | 4-phenylbenzyl |
| 3 | 4-phenylbenzyl | 3 | 1890, M + 1 | 9.03 | 4 | H |
| 4 | (10-undecen-1-yl) | 4 | 2032, M + 4 | 12.68 | 10 | =$R^1$ |
| 5 | 4-butylbenzyl | 1 | 2018, M + 3 | 11.26 | 9 | =$R^1$ |
| 6 | 2-naphthylmethyl | 1 | 2006, M + 3 | 10.42 | 12 | =$R^1$ |
| 7 | 4-(2-phenylvinyl)-benyzl | 1 | 1917, M + 2 | 10.47 | 3 | H |
| 8 | 4-(2-phenylvinyl)-benyzl | 1 | 2109, M + 1 | 11.82 | 7 | =$R^1$ |
| 9 | 4-chlorobenzyl | 1 | 1977, M + 6 | 9.27 | 13 | =$R^1$ |
| 10 | 4-phenoxybenyzl | 1 | 2090, M + 3 | 10.97 | 19 | =$R^1$ |
| 11 | 3-phenoxybenzyl | 1 | 2090, M + 3 | 10.94 | 12 | =$R^1$ |
| 12 | 4-pentyloxybenzyl | 1 | 2080, M + 4 | 11.96 | 15 | =$R^1$ |
| 13 | 4-(trifluoromethoxy)-benzyl | 1 | 2074, M + 3 | 12.55 | 14 | =$R^1$ |
| 14 | 4-(trifluoromethoxy)-benzyl | 1 | 1899, M + 2 | 10.34 | 4 | H |
| 15 | 3,5,5-trimethylhexyl | 4 | 1980, M + 4 | 11.34 | 3 | =$R^1$ |

The present teicoplanin derivatives are useful for the treatment of bacterial infections. Therefore, in another embodiment, the present invention is directed to a method for controlling a bacterial infection in a host animal, typically a warm-blooded animal, which comprises administering to the host animal an effective, antibacterial amount of a compound of the present invention. In this embodiment, the compounds can be used to control and treat infections due to various bacteria, but especially gram-positive bacteria. In a preferred embodiment, the teicoplanin derivatives are used to control and treat infections due to bacteria resistant to existing antibacterials. For example, certain bacteria are resistant to methicillin, and yet others are resistant to vancomycin and/or teicoplanin. The present compounds provide a technique for controlling and treating infections due to such resistant bacterial species.

In carrying out this embodiment of the invention, the compounds can be administered by any of the conventional techniques, including the oral route and parenteral routes such as intravenous and intramuscular. The amount of compound to be employed is not critical and will vary depending on the particular compound employed, the route of administration, the severity of the infection, the interval between dosings, and other factors known to those skilled in the art. In general, a dose of from about 0.5 to about 100 mg/kg will be effective; and in many situations, lesser doses of from about 0.5 to about 50 mg/kg will be effective. A compound of the present invention can be administered in a single dose, but in the known manner of antibacterial therapy, a compound of the present invention is typically administered repeatedly over a period of time, such as a matter of days or weeks, to ensure control of the bacterial infection.

Also in accordance with known antibacterial therapy, a compound of the present invention is typically formulated for convenient delivery of the requisite dose. Therefore, in another embodiment, the present invention is directed to a pharmaceutical formulation comprising a compound of the present invention, in combination with a pharmaceutically-acceptable carrier. Such carriers are well known for both oral and parenteral routes of delivery. In general, a formulation will comprise a compound in a concentration of from about 0.1 to about 90% by weight, and often from about 1.0 to about 3%.

The antibacterial efficacy of the present teicoplanin derivatives is illustrated by the following tables. The minimal inhibitory concentrations (MICs) were determined using a standard broth micro-dilution assay. TABLES 2A, 2B, and 2C present MICs against individual organisms. TABLE 3 presents a comparison of the activity of illustrative compounds against representative vancomycin-resistant and vancomycin-sensitive enterococci (*Enterococcus faecium* and *Enterococcus faecalis,* mean geometric MIC (mcg/mL), as determined by the standard broth micro-dilution assay. In TABLES 2A and 2B, "N.G" stands for "no growth", indicating that the microorganism failed to grow in the control.

TABLE 2A

| Ex # | S. aureus 446 | S. aureus 489 | S. aureus 447 | S. aureus X400 | S. aureus X778 | S. aureus 491 | S. aureus S13E | S. aureus SA1199 |
|---|---|---|---|---|---|---|---|---|
| 1 | 0.5 | 0.125 | 2 | 0.25 | 0.25 | 0.25 | 0.25 | 0.25 |
| 2 | ≦.03 | ≦.03 | 0.25 | ≦.03 | 0.125 | ≦.03 | ≦.03 | ≦.03 |
| 4 | 4 | 2 | 8 | 2 | 4 | 4 | 2 | |
| 5 | 0.5 | 0.5 | 0.5 | 0.25 | 0.25 | 0.25 | 1 | 0.25 |
| 6 | ≦.06 | ≦.06 | ≦.06 | ≦.06 | ≦.06 | ≦.06 | ≦.06 | ≦.06 |
| 7 | 2 | 0.25 | 2 | 0.5 | 2 | 1 | 0.5 | |
| 8 | 1 | 0.25 | 1 | 1 | 2 | 1 | 2 | 4 |
| 9 | ≦0.06 | ≦0.06 | 4 | ≦0.6 | ≦0.6 | ≦0.6 | 0.25 | 0.125 |
| 10 | 0.25 | 0.5 | 1 | 0.25 | 0.5 | 1 | 2 | 2 |
| 11 | 2 | 1 | 1 | 0.5 | 0.25 | 0.25 | 2 | 0.5 |
| 12 | 4 | 2 | 16 | 2 | 4 | 2 | 2 | |
| 13 | 1 | 0.5 | 1 | 0.5 | 1 | 0.5 | 1 | |
| 14 | 4 | 2 | 8 | 2 | 4 | 2 | 2 | |
| 15 | 1 | 2 | 16 | 2 | 2 | 2 | 2 | |

TABLE 2B

| Ex # | S. aureus SA1199R | S. aureus SA1199B | S. h. 105 | S. h. 415 | S. epi 270 | E. f. 180 | E. f. 180-1 | E. f. 2041 |
|---|---|---|---|---|---|---|---|---|
| 1 | ≦.06 | 0.5 | ≦.06 | 4 | 1 | ≦06 | ≦.06 | ≦.06 |
| 2 | ≦.03 | ≦.03 | 0.25 | 8 | 0.25 | 32 | 0.25 | ≦.03 |
| 4 | | | 16 | 16 | 2 | 8 | | |
| 5 | ≦.06 | 0.25 | 0.125 | 4 | 0.25 | ≦.06 | ≦.06 | ≦.06 |
| 6 | ≦.06 | ≦.06 | ≦.06 | 4 | ≦.06 | 0.25 | ≦.06 | ≦.06 |
| 7 | | | 0.25 | 32 | 2 | 64 | 1 | 0.25 |
| 8 | 0.125 | 2 | >64 | >64 | 1 | 0.25 | 0.125 | 0.125 |
| 9 | ≦.06 | ≦.06 | 8 | 16 | 0.125 | 64 | ≦.06 | ≦.06 |
| 10 | ≦.06 | 0.5 | >64 | 8 | 0.5 | 0.25 | ≦.06 | ≦.06 |
| 11 | ≦.06 | 0.25 | >64 | 16 | ≦.06 | 1 | 0.25 | ≦.06 |
| 12 | | | 32 | 64 | 4 | 8 | N.G. | N.G. |
| 13 | | | 32 | 8 | 0.5 | 4 | N.G. | N.G. |
| 14 | | | 1 | >128 | 2 | >128 | 8 | 8 |
| 15 | | | 16 | 8 | 4 | 8 | N.G. | N.G. |

TABLE 2C

| Ex # | E. f. 276 | E. gall. 245 | M. cat M12 | H. influ RD | H. influR D/BL+ | EC14 | St. pneu mo P1 | St. pyro C203 |
|---|---|---|---|---|---|---|---|---|
| 1 | ≦.06 | ≦.06 | ≦.06 | 64 | 64 | >64 | ≦.06 | ≦.06 |
| 2 | ≦.03 | 0.25 | 0.25 | 16 | 32 | >32 | ≦.03 | ≦.03 |
| 4 | | | | | | >128 | 1 | 0.5 |
| 5 | ≦.06 | ≦.06 | ≦.06 | 64 | 1 | >64 | ≦.06 | ≦.06 |
| 6 | ≦.06 | ≦.06 | ≦.06 | 16 | 1 | >64 | ≦.06 | ≦.06 |
| 7 | | | | | | >128 | ≦.06 | 0.25 |
| 8 | 0.5 | 0.25 | 0.25 | N.G. | N.G. | >64 | 0.25 | 0.125 |
| 9 | ≦.06 | ≦.06 | ≦.06 | N.G. | N.G. | >64 | ≦.06 | ≦.06 |
| 10 | 0.5 | 0.25 | ≦.06 | N.G. | N.G. | >64 | 0.125 | ≦.06 |
| 11 | 0.25 | 0.125 | ≦.06 | N.G. | N.G. | >64 | ≦.06 | ≦.06 |
| 12 | | | | | | >128 | 2 | 0.5 |
| 13 | | | | | | >128 | 0.05 | ≦.06 |
| 14 | | | | | | >128 | 1 | 1 |
| 15 | | | | | | >128 | 0.5 | 0.25 |

TABLE 3

| Ex # | Resist. MIC | Sens. MIC |
|---|---|---|
| 1 | 3.4 | 0.14 |
| 1 | 0.86 | 0.046 |
| 2 | >32 | 2.6 |
| 3 | >64 | 4.6 |
| 4 | 1.2 | 1.5 |
| 5 | 0.84 | 0.25 |
| 6 | 3.4 | 0.11 |
| 7 | 19.03 | 0.76 |
| 8 | 0.59 | 0.22 |
| 9 | 13 | 0.11 |
| 10 | 1.7 | 0.19 |
| 11 | 3.4 | 0.11 |
| 12 | 0.84 | 0.38 |
| 13 | 45 | 0.25 |
| 14 | >32 | 5.28 |
| 15 | 0.59 | 0.33 |

We claim:

1. A compound of the formula:

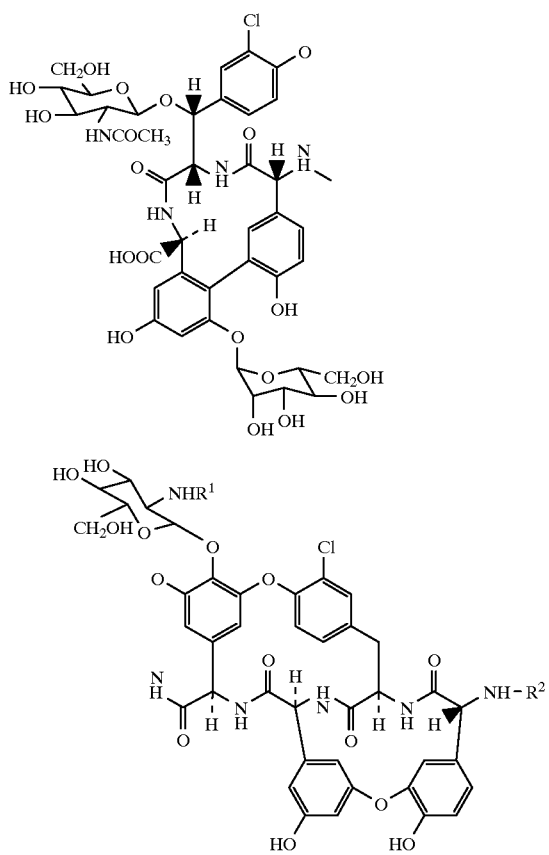

wherein one of $R^1$ and $R^2$ is:

—$CH_3$, —$CH_2$—($C_1$–$C_{11}$ alkyl), —$CH_2$—($C_2$–$C_{11}$ alkenyl), —$CH_2$—($C_2$–$C_{11}$ alkynyl), cycloalkylmethyl of the formula:

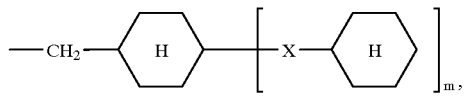

where X is a linker of the formula —$(CH_2)_x$—Z—$(CH_2)_y$—
wherein each of x and y is 0–6,
and the sum of x and y=0–6,
Z is a bond, —O—, —S—, —CH=CH—, or —C≡C—, and
m is 0 or 1;
naphthylmethyl,
thienylbenzyl,
phenylthienylmethyl,
benzyl of the formula:

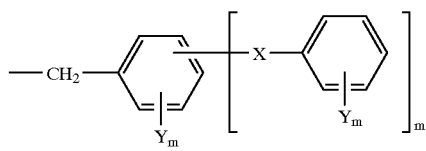

wherein X is the same as defined above
and any Y is independently halo, loweralkyl of $C_1$–$C_5$, loweralkoxy of $C_1$–$C_5$, loweralkylthio of $C_1$–$C_5$, trifluoromethyl, or trifluoromethoxy, and each m is independently 0 or 1;
and the other of $R^1$ and $R^2$ is identical or is H, or, in the case of $R^2$, an amino protecting group, or a pharmaceutically acceptable salt thereof.

2. A compound of claim 1 wherein at least one of $R^1$ or $R^2$ is

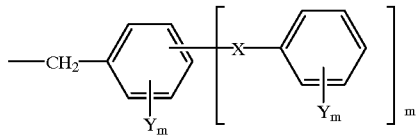

as defined.

3. A compound of claim 1 wherein $R^1$=$R^2$.

4. A pharmaceutical formulation comprising a compound of claim 1 in combination with a pharmaceutically acceptable carrier.

5. A method for treating a bacterial infection in a host comprising the step of administering to the host an effective amount of a formulation of claim 4.

6. A method of claim 5 in which the bacterial infection is attributable to a vancomycin-resistant-enterococcus.

7. A method for treating a bacterial infection in a host comprising the step of administering to said host an effective amount of a compound according to claim 1.

8. The method of claim 7 wherein said compound exhibits activity against vancomycin-resistant-enterococcus.

9. A process for the preparation of a compound of claim 1 which comprises reductively alkylating deacyl teicoplanin or an $N^{15}$-amino protected teicoplainin, and thereafter optionally forming a pharmaceutically-acceptable salt thereof or removing the amino protecting group, or both forming a salt and removing the amino protecting group in either order.

* * * * *